United States Patent [19]

Bauer

[11] Patent Number: 5,602,293
[45] Date of Patent: Feb. 11, 1997

[54] PROCESS FOR SEPARATING A FEEDSTOCK STREAM ESSENTIALLY CONSISTING OF HYDROGEN, METHANE AND $C_3/C_4$-HYDROCARBONS

[75] Inventor: Heinz Bauer, München, Germany

[73] Assignee: Linde Aktiengesellschaft, Wiesbaden, Germany

[21] Appl. No.: 416,844

[22] PCT Filed: May 12, 1993

[86] PCT No.: PCT/EP93/01182

§ 371 Date: Apr. 14, 1995

§ 102(e) Date: Apr. 14, 1995

[87] PCT Pub. No.: WO94/08923

PCT Pub. Date: Apr. 28, 1994

[30] Foreign Application Priority Data

Oct. 16, 1992 [DE] Germany ............. 42 35 006.9

[51] Int. Cl.[6] ................................... C07C 7/00
[52] U.S. Cl. ............. 585/800; 208/347; 208/350; 208/353; 208/358
[58] Field of Search ............. 585/800; 55/80; 208/347, 350, 353, 358

[56] References Cited

U.S. PATENT DOCUMENTS

| | | | |
|---|---|---|---|
| 3,213,154 | 10/1965 | Bauer | 585/802 |
| 4,608,068 | 8/1986 | Bauer et al. | 62/18 |
| 4,617,039 | 10/1986 | Buck | 62/26 |
| 4,673,488 | 6/1987 | Turner et al. | 585/802 |
| 5,026,095 | 6/1991 | Bauer | 585/800 |
| 5,026,952 | 6/1991 | Bauer | 585/800 |
| 5,414,188 | 5/1995 | Ha et al. | 585/800 |
| 5,414,190 | 5/1995 | Frög et al. | 585/802 |
| 5,421,165 | 6/1995 | Paradowski et al. | 585/800 |
| 5,430,223 | 7/1995 | Bauer | 585/800 |

FOREIGN PATENT DOCUMENTS

94/08923  4/1994  WIPO .

OTHER PUBLICATIONS

Dr. Heinz C. Bauer, "Cryogenic Olefins Recovery from Dehydrogenation. . .", AIChE Symposium on Cryogenic Gas Processing . . . , Mar. 29–Apr. 2, 1992.

*Primary Examiner*—Helane Myers
*Attorney, Agent, or Firm*—Millen, White, Zelano & Branigan, P.C.

[57] ABSTRACT

Process for separating a feedstock stream essentially consisting of hydrogen, methane and $C_3/C_4$-hydrocarbons, which first passes through a pretreatment, such as, e.g., dehydrogenation, after which the feedstock stream undergoes an at least one-stage partial condensation and separation into a $C_3/C_4$-hydrocarbon-rich fraction and into an $H_2/CH_4$ fraction, after which a partial stream of the $H_2/CH_4$ fraction is mixed in the not yet pretreated feedstock stream. The $H_2/CH_4$ gas fraction drawn off from first separator (S1) is divided into two partial streams (10, 17), and first partial stream (10) together with liquid fraction (11) of first separator (S1) is fed to a second separator (S2) after partial condensation (W2), $C_3/C_4$-hydrocarbon-rich liquid fraction (16), drawn off at the bottom of second separator (S2), together with the second partial stream of $H_2/CH_4$ gas fraction (17) from first separator (S1) is conveyed to a stripping column (S3), an $H_2$-rich gas fraction with high purity (13) is drawn off at the top of second separator (S2), and after evaporating in heat exchange (W2) with the process streams to be cooled is mixed with feedstock stream (2, 2a, 2b) before its pretreatment, and a $C_3/C_4$-rich product fraction (20) is drawn off at the bottom of stripping column (S3) and an $H_2$-rich gas fraction with less high purity (18) is drawn off at the top of stripping column (S3).

8 Claims, 1 Drawing Sheet

PROCESS FOR SEPARATING A FEEDSTOCK STREAM ESSENTIALLY CONSISTING OF HYDROGEN, METHANE AND C₃/C₄-HYDROCARBONS

DESCRIPTION

Process for separating a feedstock stream essentially consisting of hydrogen, methane and $C_3/C_4$-hydrocarbons.

The invention relates to a process for separating a feedstock stream essentially consisting of hydrogen, methane and $C_3/C_4$-hydrocarbons, which first passes through a pretreatment, such as, e.g., dehydrogenation, after which the feedstock stream undergoes an at least one-stage partial condensation and separation into a $C_3/C_4$-hydrocarbon-rich fraction and into an $H_2/CH_4$ fraction, after which a partial stream of the $H_2/CH_4$ fraction is mixed in the not yet pretreated feedstock stream.

Processes for separating a feedstock stream essentially consisting of hydrogen, methane and $C_3/C_4$-hydrocarbons are used, e.g., in cryogenic separation, downstream to a dehydrogenation of isobutane to isobutene, of the product stream derived from the dehydrogenation reactor. The dehydrogenation of isobutane to isobutene plays an important role above all in the production of MTBE (methyl-tert-butyl ether), since isobutene and methanol are needed for the production of MTBE. Based on increasingly stiffened exhaust gas regulations for motor vehicles, the use of MTBE, which is used as octane number improver for automotive fuels, will increase in subsequent years. But while methanol is available in sufficient amounts, a considerable deficiency of isobutene exists.

The article "Cryogenic Olefins Recovery from Dehydrogenation Reactor Effluents" by Dr. Heinz C. Bauer (presented at the AIChE Symposium on Cryogenic Gas Processing, 1992 Spring National Meeting, Mar 29–Apr. 2, 1992) provides an overview of the process possibilities for recovering $C_3/C_4$ hydrocarbon-rich product fractions available in the prior art. In this case, especially FIG. 13 shows a process for separating a feedstock stream essentially consisting of hydrogen, methane and $C_4$-hydrocarbons, in which a part of the recovered gas mixture, consisting of hydrogen and methane, is drawn off from the unit (net fuel gas) and a part is recycled into the dehydrogenation reactor (recycle gas). This recycling of a part of the gas mixture into the dehydrogenation reactor takes place to reduce an undesirable carbon-black formation in it. But this succeeds only incompletely.

According to the invention, it has now been determined that the undesirable carbon-black formation can be better suppressed the higher the hydrogen portion is in the stream recycled into the dehydrogenation reactor. Additional substances, such as, e.g., methane, represent, as the latest studies on which the invention is based have shown, only an unnecessary impurity which both blocks the capacity and worsens the economic efficiency of the process.

The purpose and object of this invention is to indicate a process in which, among others, an $H_2$-rich gas stream is recycled into the dehydrogenation and a gas stream containing components to be considered as inert impurities for the process is recovered.

This is achieved according to the invention in that the $H_2/CH_4$ gas fraction drawn off from the first separator is divided into two partial streams, and the first partial stream together with the liquid fraction of the first separator is fed to a second separator after partial condensation, the $C_3/C_4$-hydrocarbon-rich liquid fraction, drawn off at the bottom of the second separator, together with the second partial stream of the $H_2/CH_4$ gas fraction from the first separator, is conveyed to a stripping column, in that an $H_2$-rich gas fraction with high purity is drawn off at the top of the second separator, and after heating in the heat exchange with process streams to be cooled, is mixed with the feedstock stream before its pretreatment and in that a $C_3/C_4$-hydrocarbon-rich product fraction is drawn off at the bottom of the stripping column and an $H_2$-rich gas fraction with less high purity is drawn off at the top of the stripping column.

By adding the liquid bottom fraction of the first separator to the first partial stream of the $H_2/CH_4$ gas fraction drawn off from the first separator, the desired hydrogen quality in the gas fraction is already achieved in the second separator. While in the process belonging to the prior art, only the liquid $C_3/C_4$-rich bottom fractions of the individual separators are brought together, in the process according to the invention, the liquid $C_3/C_4$-rich bottom fraction of the first separator is used as solvent for the $C_3/C_4$-hydrocarbons still contained in the first partial stream. In this way, the hydrogen purity required for the recycle gas can already be achieved at higher temperatures. Moreover, in the process according to the invention, only the partial stream of the top fraction of the first separator is freed from inert components, which ultimately is fed again to the dehydrogenation reactor.

The liquid fraction drawn off at the bottom of the second separator is conveyed to a stripping column after heating and optionally partial evaporation together with the second partial stream of the $H_2/CH_4$ gas stream drawn off from the first separator. The separation into a $C_3/C_4$-rich product fraction and another $H_2$-rich gas fraction contaminated mainly with methane then takes place in the stripping column.

The $H_2$-rich recycle gas with high purity drawn off at the top of the second separator is first optionally expanded providing refrigerating power to be able to make available the peak coldness required for the process. The mechanical energy resulting in this expansion can be used, e.g., to precompress the feedstock stream. After the warming in the heat exchange with process streams to be cooled, the $H_2$-rich recycle gas is mixed with the not yet pretreated feedstock stream and recycled before the dehydrogenation.

To further develop the invention, it is proposed that the mixing of the $H_2$-rich gas fraction with high purity drawn off at the top of the second separator with the not yet pretreated feedstock stream takes place on at least two different temperature levels.

The supply of coldness of the entire process takes place in an energetically useful way by evaporating the liquid, not yet pretreated feedstock stream. In this case, the evaporation is generally performed in several stages. The mixing of the not yet pretreated feedstock stream with the expanded $H_2$-rich gas stream from the second separator does not take place all at once, e.g., at the lowest temperature level, but in several stages. As a result, the condensation of the feedstock stream occurring at sliding temperature is better sustained.

Another configuration of the process according to the invention is characterized in that below the top of the stripping column, an $H_2$-rich gas fraction is drawn off, partially condensed and provided again on the top of the column above the drawing-off point.

A reduction of the $C_3/C_4$ product losses at the bottom of the stripping column is achieved by this configuration of the process according to the invention.

BRIEF DESCRIPTION OF THE DRAWING

The invention as well as further configurations of the invention are represented based on the embodiment of FIG. 1.

A gas mixture consisting of 95.2% i-$C_4H_{10}$, 2.9% $C_4H_{10}$ and 1.9% other components (all data relate to mol %) at a temperature of 43.0° C. and a pressure of 10.7 bars is conveyed to the process by pipe 1. The feedstock stream is now evaporated in the two heat exchangers W1 and W2 to prepare the process coldness and then mixed in the expanded $H_2$-rich gas in pipe 3 (this will be considered later on in more detail). This admixing takes place usefully at three different temperature levels, namely in heat exchanger W1 (by pipe 2a), between two heat exchangers W1 and W2 (by pipe 2b) and after or in heat exchanger W2 (by pipe 2). The equalization of the three mixing possibilities takes place by means of valves V1, V2 and V3. The feedstock stream now essentially containing hydrogen, methane and $C_4$-hydrocarbons (44.6% $H_2$, 5.8% $CH_4$, 47.2% i-$C_4H_{10}$ and 2.4% other components) is heated in heat exchangers W2 and W1 and conveyed by pipe 4 at a temperature of 50.7° C. and a pressure of 2.5 bars to dehydrogenation reactor 5. The feedstock stream exiting from dehydrogenation reactor 5 is first fed by pipe 6 to a compressing and drying unit 7 and then conveyed by pipe 8 with a composition of 51.7% $H_2$, 9.0% $CH_4$, 19.3% i-$C_4H_{10}$, 15.8% i-$C_4H_8$ and 4.2% other components and at a temperature of 54° C. and a pressure of 6.6 bars to heat exchanger W1. This stream is partially condensed in it and then supplied to separator S1 by pipe 9. At the top of separator S1, a gaseous fraction with a composition of 84.8% $H_2$, 13.8% $CH_4$ and 2.4% other components and at a temperature of −67° C. and a pressure of 6.5 bars is drawn off and the liquid fraction from separator S1 is admixed by pipe 10. This liquid fraction consists of 48.7% i-$C_4H_{10}$, 39.8% i-$C_4H_8$ and 11.5% other components. After a cooling in heat exchanger W2 to −116.3° C., this partially condensed stream is conveyed by pipe 12 at a pressure of 6.3 bars to separator S2. A separation into a gas fraction, consisting of 88.5% $H_2$ and 11.5% $CH_4$, as well as into a liquid fraction, consisting of 47.0% i-$C_4H_{10}$, 4.5% $CH_4$, 38.4% i-$C_4H_8$ and 10.1% other components takes place in it. At the top of separator S2, the gas fraction is drawn off by pipe 13, warmed in heat exchanger W2 and fed to turboexpander T1 by pipe 14. For the sake of simplicity, only one turboexpander is represented in the figure; but it is obvious to one skilled in the art that a multistage expansion also can occur. The $H_2$-rich gas fraction is expanded in turboexpander T1 to a pressure of 2.5 bars and then fed by pipe 3 to the first of three admixing points of the not yet pretreated feedstock stream. The $C_4$-hydrocarbon-rich liquid fraction drawn off at the bottom of separator S2 is conveyed by pipe 16 into heat exchanger W2, heated in it and then expanded by valve V4 in the central area of stripping column S3. In addition to this fraction, the second part of the $H_2$-rich gas fraction, drawn off at the top of first separator S1, is fed to the area of the bottom of stripping column S3 by pipe 17 and valve V5. An $H_2$-rich, $CH_4$-containing gas fraction accumulates at the top of stripping column S3. The fraction is fed by pipe 18 to heat exchangers W2 and W1, heated in the latter in the heat exchange with process streams to be cooled and then drawn off from the unit by pipe 19 with a composition of 80.0% $H_2$, 19.3% $CH_4$ and 0.7% other components and at a temperature of 50.7° C. and a pressure of 5.6 bars. The $C_4$-rich fraction accumulating at the bottom of stripping column S3 is expanded by pipe 20 and valve V5 in separator S4. A gas fraction with a composition of 32.9% $H_2$, 59.7% $CH_4$ and 7.4% other components and at a temperature of −71.7° C. and a pressure of 0.1 bar is drawn off by pipe 21 at the top of separator S4. It can optionally be conveyed to pipe 6 between dehydrogenation reactor 5 and compressing and drying unit 7. A liquid product fraction with a composition of 2.2% $C_3H_6$, 4.3% $C_3H_8$, 48.8% i-$C_4H_{10}$, 39.8% i-$C_4H_8$ and 4.9% other components accumulates at the bottom of separator S4, which leaves the unit by pipe 24 after compression 23 to a pressure of 10.9 bars and heating in heat exchange W1 with process streams to be cooled to a temperature of 40.5° C. To increase the purity of the fractions drawn off at the top or bottom of stripping column S3, a reflux is provided in addition at the top of stripping column S3 (not represented in the figure). In this case, an $H_2$-rich gas fraction is drawn off below the top of stripping column S3, partially condensed in the heat exchange with a partial stream of the $C_4$-rich stream drawn off from pipe 16 in front of heat exchanger W2 and provided again at the top of stripping column S3 above the drawing-off point. This additional reflux is used to improve the rectification properties of stripping column S3 and makes possible an almost complete stripping of methane from the mixture stream fed to stripping column S3 by pipe 16.

Figure 1:
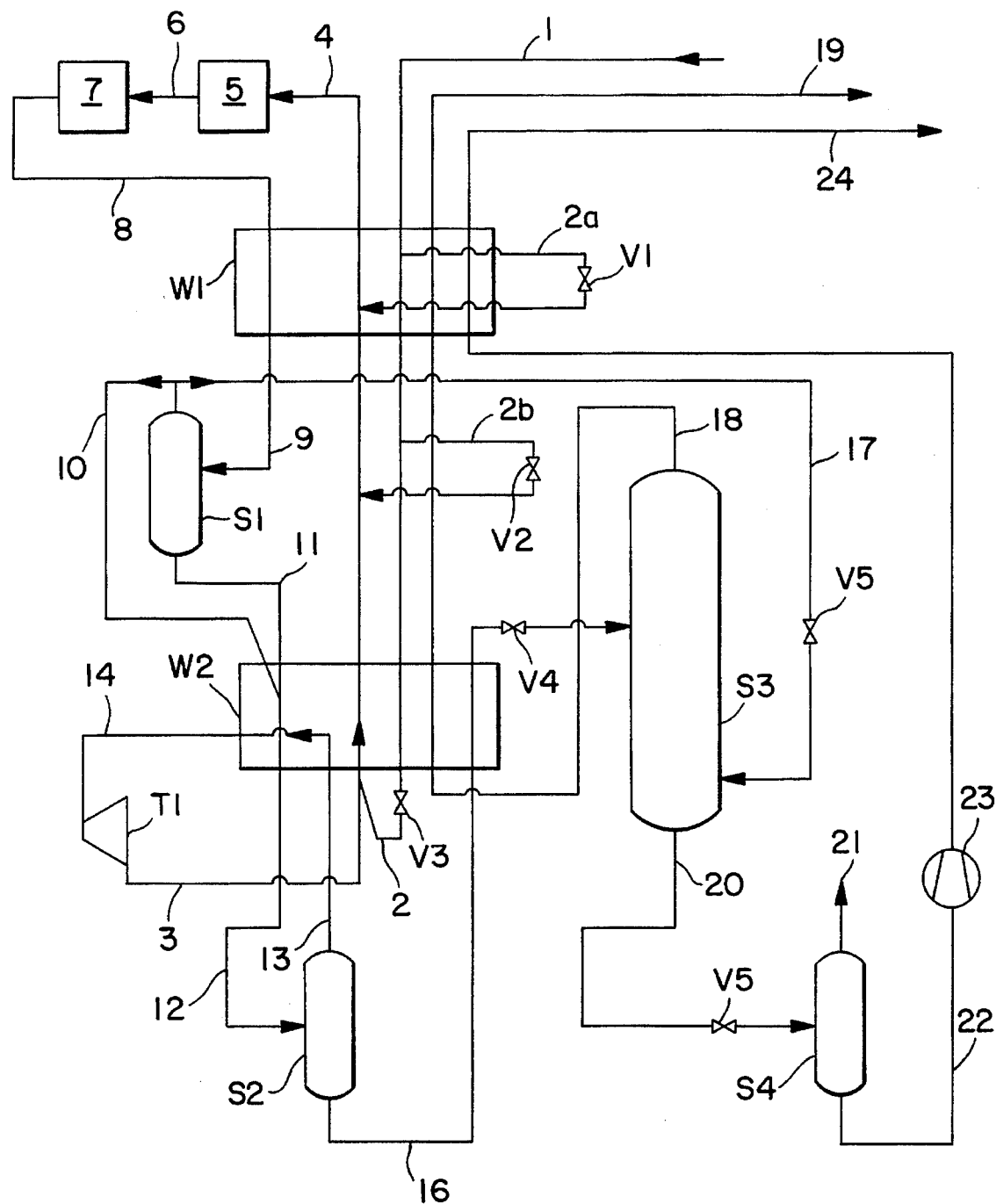

I claim:

1. In a process for separating a raw feedstock stream consisting essentially of hydrogen, methane and $C_3/C_4$-hydrocarbons, comprising in a pretreatment step, dehydrogenating said raw feedstock in a dehydrogenation reactor (5) to convert isobutane to isobutene; partially condensing the pretreated feedstock stream in at least one partial condensation stage; separating the partially condensed stream into a $C_3/C_4$-hydrocarbon-rich fraction (16) and into an $H_2/CH_4$ fraction (14); and mixing an at least partial stream of the $H_2/CH_4$ fraction with the raw feedstock stream prior to said pretreatment step, the improvement wherein said pretreated feedstock stream is partially condensed in at least two partial condensation stages (W1)(W2), said improvement further comprising;

(a) withdrawing an $H_2/CH_4$ gas fraction and a liquid fraction (11) from a first separator (S1); and dividing the latter gas fraction into first and second partial streams (10, 17);

(b) mixing said first partial stream (10) together with said liquid fraction (11) from first separator (S1); partially condensing the resultant mixture and passing the resultant partial condensate to a second separator (S2), to separate a $C_3/C_4$-hydrocarbon-rich liquid fraction (16) at the bottom of the second separator (S2) and a high purity $H_2$-rich gas fraction at the top;

(c) mixing said $C_3/C_4$ hydrocarbon-rich liquid fraction (16) from the bottom of the second separator with the second partial stream of $H_2/CH_4$ gas fraction (17) from the first separator (S1) and passing the resultant mixture to a stripping column (S3);

(d) withdrawing a $C_3/C_4$-rich product fraction (20) from the bottom of the stripping column (S3), and withdrawing an $H_2$-rich gas fraction (18) from the top of stripping column (S3), the latter $H_2$-rich gas fraction having a lower purity than said high purity $H_2$-rich gas fraction; and (e) heating said high purity $H_2$-rich gas fraction (13) from the top of second separator (S2) in heat exchange with process streams to be cooled, and mixing the resultant heated high purity $H_2$-rich gas fraction with said raw feedstock stream (2, 2a, 2b) upstream of said pretreatment, whereby the high purity of the $H_2$-rich gas leads to a superior suppression of carbon black formation in the dehydrogenating step as compared to a less pure $H_2$-rich gas.

2. Process according to claim 1, wherein the $H_2$-rich gas fraction with high purity (13) drawn off at the top of second separator (S2) is expanded providing refrigerating power (T1).

3. A process according to claim 2, wherein the mixing of the $H_2$-rich gas fraction with high purity (13) drawn off at the top of second separator (S2) with feedstock stream (2, 2a, 2b) takes place on at least two different temperature levels.

4. A process according to claim 2, wherein an $H_2$-rich gas fraction is drawn off below the top of stripping column (S3), partially condensed and is provided again to the top of column (S3) above the drawing-off point.

5. A process according to claim 4, wherein an $H_2$-rich gas fraction is drawn off below the top of stripping column (S3), partially condensed and is provided again to the top of column (S3) above the drawing-off point.

6. Process according to claim 1, wherein the mixing of the $H_2$-rich gas fraction with high purity (13) drawn off at the top of second separator (S2) with feedstock stream (2, 2a, 2b) takes place on at least two different temperature levels.

7. Process according to claim 1, wherein an $H_2$-rich gas fraction is drawn off below the top of stripping column (S3), partially condensed and is provided again to the top of column (S3) above the drawing-off point.

8. In a process for separating a raw feedstock stream consisting essentially of hydrogen, methane and $C_3/C_4$-hydrocarbons, comprising in a pretreatment step, dehydrogenating said raw feedstock in a dehydrogenation reaction (5) to convert isobutane to isobutene; partially condensing the pretreated feedstock stream in at least one partial condensation stage; separating the partially condensed stream into a $C_3/C_4$-hydrocarbon-rich fraction (16) and into an $H_2/CH_4$ fraction (14); and mixing an at least partial stream of the $H_2/CH_4$ fraction with the raw feedstock stream prior to said pretreatment step, the improvement wherein said pretreated feedstock stream is partially condensed in at least two partial condensation stages (W1)(W2), said improvement further comprising;

(a) withdrawing an $H_2/CH_4$ gas fraction and a liquid fraction (11) from a first separator (S1); and dividing the latter gas fraction into first and second partial streams (10, 17);

(b) mixing said first partial stream (10) together with said liquid fraction (11) from first separator (S1), partially condensing the resultant mixture and passing the resultant partial condensate to a second separator (S2), to separate a $C_3/C_4$-hydrocarbon-rich liquid fraction (16) at the bottom of the second separator (S2) and a high purity $H_2$-rich gas fraction at the top; and (c) mixing the resultant high purity $H_2$-rich gas fraction with said raw feedstock stream (2, 2a, 2b) upstream of said pretreatment, whereby the high purity of the $H_2$-rich gas leads to a superior suppression of carbon black formation in the dehydrogenating step as compared to a less pure $H_2$-rich gas.

* * * * *